United States Patent [19]

Roychowdhury

[11] Patent Number: 5,587,125

[45] Date of Patent: Dec. 24, 1996

[54] NON-COEXTRUSION METHOD OF MAKING MULTI-LAYER ANGIOPLASTY BALLOONS

[75] Inventor: Suranjan Roychowdhury, Minnetonka, Minn.

[73] Assignee: Schneider (USA) Inc., Minneapolis, Minn.

[21] Appl. No.: 290,075

[22] Filed: Aug. 15, 1994

[51] Int. Cl.⁶ .................................. B29C 49/22
[52] U.S. Cl. ........................ 264/515; 264/512; 604/96; 606/194
[58] Field of Search .................... 264/512, 514, 264/515, 516, 292, 269, 266, 171.12; 604/96; 606/192, 194; 156/308.2, 287, 285

[56] References Cited

U.S. PATENT DOCUMENTS

| | | | |
|---|---|---|---|
| 3,449,792 | 6/1969 | Plummer | 264/535 |
| 4,490,421 | 12/1984 | Levy | 604/96 |
| 4,775,371 | 10/1988 | Mueller, Jr. . | |
| 4,952,357 | 8/1990 | Euteneuer . | |
| 5,087,394 | 2/1992 | Keith | 264/291 |
| 5,195,969 | 3/1993 | Wang et al. | 604/96 |
| 5,207,700 | 5/1993 | Euteneuer . | |
| 5,270,086 | 12/1993 | Hamlin . | |
| 5,290,306 | 3/1994 | Trotta et al. | 606/194 |
| 5,358,486 | 10/1994 | Saab | 604/96 |

FOREIGN PATENT DOCUMENTS

| | | |
|---|---|---|
| 0457456A1 | 11/1991 | European Pat. Off. . |
| 0553960A1 | 8/1993 | European Pat. Off. . |
| 58-187319 | 11/1983 | Japan ................ 264/516 |
| WO9219316 | 11/1992 | WIPO . |

*Primary Examiner*—Catherine Timm
*Attorney, Agent, or Firm*—Haugen and Nikolai, P.A.

[57] ABSTRACT

A non-coextrusion process for making multi-layer angioplasty balloons involves pre-forming separate parisons and then concentrically disposing the plural parisons to form a composite parison which is then subjected to a blow-molding process. The resulting balloon can have its properties tailored by appropriate selection of the particular plastics to be used for the multiple parisons.

18 Claims, 2 Drawing Sheets

A — EXTRUDE 1st. TUBULAR PARISON OF A FIRST POLYMERIC MAT'L TO A PREDETERMINED LENGTH, I.D. AND WALL THICKNESS.

B — EXTRUDE 2nd. TUBULAR PARISON OF A 2nd. POLYMERIC MAT'L TO A PREDETERMINED LENGTH LESS THAN OR EQUAL TO THAT OF THE 1st. TUBULAR PARISON AND OF AN I.D. GREATER THAN THE O.D. OF THE 1st. TUBULAR PARISON.

C — COAXIALLY DISPOSE THE 2nd TUBULAR PARISON OVER THE 1st TUBULAR PARISON.

D — HEAT THE PRODUCT OF STEP C TO A TEMPERATURE ABOVE THE TRANSITION TEMPERATURE OF THE POLYMERIC MATERIALS.

E — SUBJECT THE PRODUCT OF STEP D TO A STRETCH/BLOW-MOLDING OPERATION TO YIELD A MULTI-LAYER EXPANDER MEMBER.

A — EXTRUDE 1st. TUBULAR PARISON OF A FIRST POLYMERIC MAT'L TO A PREDETERMINED LENGTH, I.D. AND WALL THICKNESS.

B — EXTRUDE 2nd. TUBULAR PARISON OF A 2nd. POLYMERIC MAT'L TO A PREDETERMINED LENGTH LESS THAN OR EQUAL TO THAT OF THE 1st. TUBULAR PARISON AND OF AN I.D. GREATER THAN THE O.D. OF THE 1st. TUBULAR PARISON.

C — COAXIALLY DISPOSE THE 2nd TUBULAR PARISON OVER THE 1st TUBULAR PARISON.

D — HEAT THE PRODUCT OF STEP C TO A TEMPERATURE ABOVE THE TRANSITION TEMPERATURE OF THE POLYMERIC MATERIALS.

E — SUBJECT THE PRODUCT OF STEP D TO A STRETCH/BLOW-MOLDING OPERATION TO YIELD A MULTI-LAYER EXPANDER MEMBER.

FIG. 1

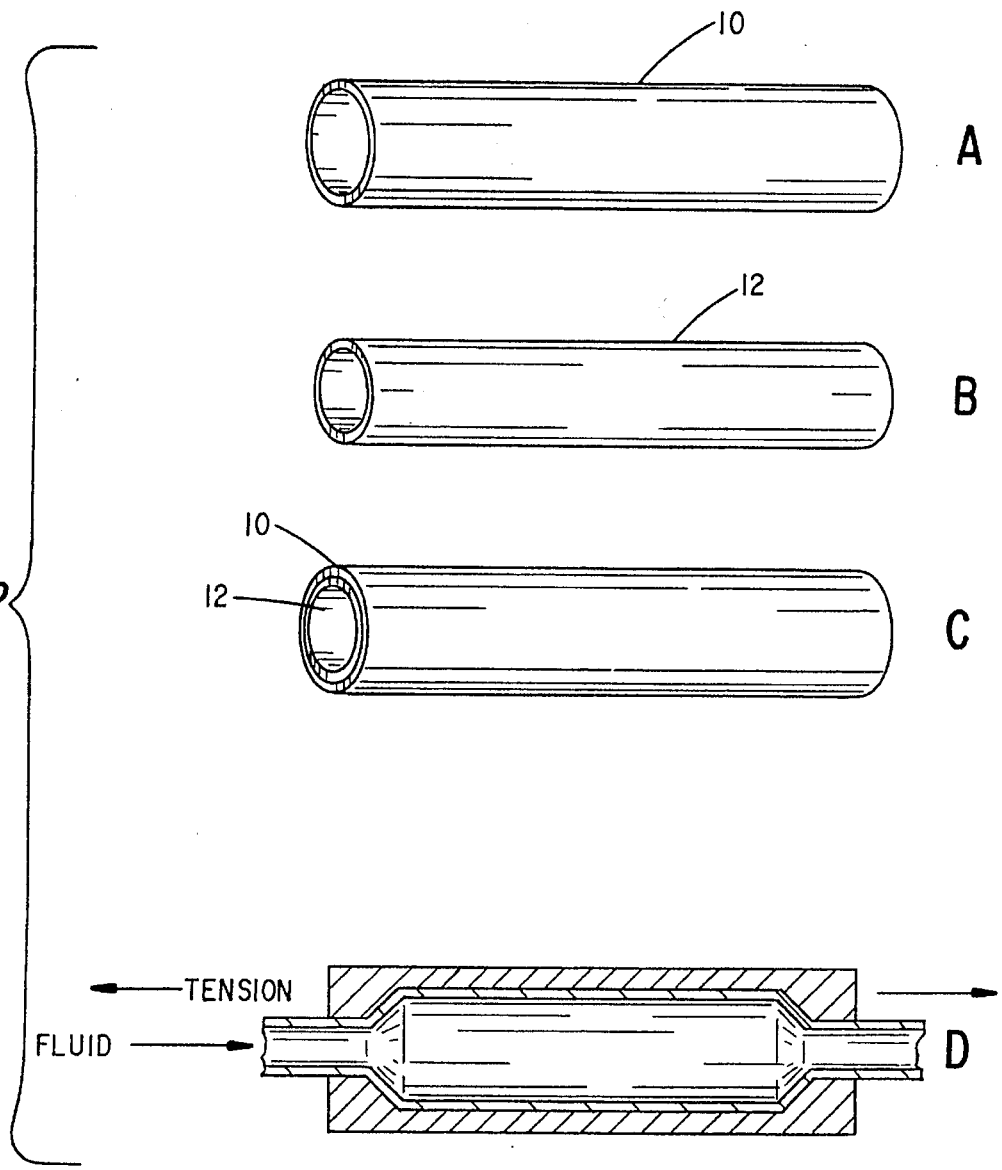

NON-COEXTRUSION METHOD OF MAKING MULTI-LAYER ANGIOPLASTY BALLOONS

BACKGROUND OF THE INVENTION

I. Field of the Invention:

This invention relates generally to balloon catheters and more particularly to methods for fabricating a multi-layer balloon composite exhibiting enhanced characteristics attributable to the properties of the individual layers comprising the balloon.

II. Discussion of the Prior Art:

In the Hamlin patent 5,270,086, there is described a method for fabricating multi-layer composite expander members (balloons) for use on angioplasty and other types of balloon catheters. As is pointed out in the Hamlin patent, by selective choice of the materials comprising the individual layers on the multi-layer balloon, the characteristics on the resulting balloon product can be tailored to overcome drawbacks of various polymer materials that have been used in the past in creating single layer balloons. For example, a balloon fabricated from polyethylene terethphalate exhibits excellent burst strength and rupture properties with a desirable low distensibility, but it is difficult to bond such a balloon to a catheter body. By first extruding a tubular parison from a polymeric material having good thermal bonding properties relative to the material of the catheter on which it is used and then co-extruding a layer of polyethylene terethphalate (PET) on that parison, when the composite is subjected to a stretch blow-molding operation in a heated mold, a balloon results that allows ready thermal bonding to a catheter body.

It is also a desirable property of a expander member for an angioplasty catheter that its surface be lubricous. Lubricity may be added to a PET balloon by forming a three-layer tubular parison where, for example, PET is the intermediate layer provided for its high burst strength, low distensibility and known rupture characteristics, an inner polyethylene layer to enhance bondability to a catheter body, and an co-extruded outer layer of a polymer, such as polycaprolactam, which is hydrophilic and exhibits low frictional resistance when passed through the vascular system.

Further information concerning the advantages and properties of co-extruded expander members for medical catheters are set forth in published Patent Cooperation Treaty application WO92/19316 and published European application 553,960A1.

The formation of multi-layer balloons using co-extrusion processes often times results in high rejection rates. It is somewhat difficult to maintain uniform layer thicknesses which may result in unacceptable variations in the wall thickness of the resulting balloons once they are formed in a stretch blow-molding operation. Moreover, once parisons for the fabrication of multi-layer expander members are manufactured using a co-extrusion process, the number of layers, their thicknesses and relative positions are fixed. The only way to vary these parameters would be to carry out additional extrusion runs, which is both time-consuming and expensive. In that each extrusion run generates a certain minimum quantity of parison lengths, process iterations cause manufacturing costs to escalate rapidly. It can also be appreciated that the prior art co-extrusion processes are quite inflexible in terms of being able to step through a number of possible multi-layer configurations quickly. Finally, co-extrusion is recognized as a more expensive process than the standard, single polymer extrusion process.

The method of the present invention obviates many of the foregoing drawbacks of the prior art co-extrusion processes for fabricating expander members for angioplasty and other medical catheters. Specifically, following the methods of the present invention materially increases the yield of acceptable multi-layer balloons without materially increasing the manufacturing cost thereof.

SUMMARY OF THE INVENTION

Rather than creating parisons for multi-layer expander members for use with medical catheters using co-extrusion techniques, in accordance with the present invention a first plurality of tubular parisons, made of a polymeric material having first physical properties, are formed in a single layer extrusion process with the extruded material having predetermined I.D. and wall thickness dimensions and being cut into multiple segments of desired lengths. A second plurality of tubular parison, made of a polymer or polymer blend having second physical properties and dimensions is likewise formed in a single layer extrusion process. The outer diameter of the second plurality of parisons is greater than the outer diameter of the first plurality of tubular parison and the I.D. of the latter is slightly greater than the O.D. of the first set of parisons. One of the second group of tubular parisons is then concentrically disposed in telescoping relation with respect to one of the first tubular parison to form a composite parison. If desired, other tubular parisons may be similarly formed and coaxially disposed about the first two in creating a three layer configuration. The composite parison is heated and then subjected to a blow-molding operation in a mold to form a multi-layer expander member. The heating of the composite parison and expansion of this parison in the mold acts to thermally bond the adjacent layers of the multi-layer expander member to one another.

In accordance with a second manufacturing method, a multi-layer expander member for an angioplasty catheter is formed by first coaxially placing an outer polymeric sleeve of a length corresponding to the size of the balloon to be formed over a second, longer, extruded parison having a predetermined outer diameter. The polymers chosen for the inner and outer tubes will typically exhibit differing physical properties. The composite parison is then heated to a predetermined temperature prior to or when placed in a split mold, at which point a fluid is blown into the inner parison to radially expand it as it is longitudinally stretched within the mold to expand both it and the surrounding outer sleeve to biaxially orient the inner member and bond the inner and outer members together in creating a multi-layer expander member.

Those skilled in the art can appreciate that the method of the present invention offers significantly greater flexibility than the prior art co-extrusion process in that it permits mixing and matching of layers by selecting a series of preformed single layer parisons. Further, the number and thicknesses of the layers can be easily varied by judiciously selecting pre-formed, single layer parisons and placing them in a coaxial relationship prior to the blow-molding operation. Thus, design optimization to identify the optimum multi-layer configuration can be carried out quickly. Hence, design changes are readily achieved.

The entire rationale of the co-extrusion step in the formation of a parison to be used in creating a multi-layer expander member for an angioplasty catheter or the like is to bond multiple layers together into a single entity or parison. This is a separate and distinct step before that of actually blowing a multi-layer balloon. In accordance with the present invention, the joining of the various layers together and the blowing of the expander member itself preferably occurs in a single step.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which:

FIG. 1 depicts a process flow chart illustrating the steps in creating a multi-layer expander member for a "balloon" catheter in accordance with the present invention; and FIG. 2 illustrates the manner in which the method of FIG. 1 is implemented.

DESCRIPTION OF THE PREFERRED EMBODIMENTS

Referring to the process flow diagram of FIG. 1 and the greatly enlarged views of FIG. 2, the first step in the process is to create a first tubular parison 10 of a first polymeric material having a predetermined length, I.D. and wall thickness. This step may be carried out by extruding a tube of the first material so that it possesses a desired inner diameter (I.D.) and wall thickness and then cutting the extruded tube to desired lengths for installation in a stretch/blow-molding fixture. Alternatively, a tube of the desired material may be extruded, cut to a given length and then mounted on a mandrel and necked down by stretching the tube on the mandrel until the desired I.D. and wall thickness are achieved. Without limitation, the wall thickness of the first tubular parison may be in the range of from 0.018 to 0.030 inch and a wall thickness variation less than 10% and preferably between about 3% and 0%.

The particular polymeric material chosen for the first or outer tubular parison 10 is based upon the desired physical properties for the innermost layer of the expander member to be formed. For example, if a polyester, such as PET, is to be used as the material for one of the layers of the composite expander member to be formed because of its desirable burst strength and rupture properties, and the expander member is to be affixed to a catheter body comprising a polyether block amide (PEBA), to enhance the bondability of the composite balloon to the catheter body, the plastic of the innermost layer may, for example, be polyvinyl chloride which more readily bonds to each.

As is illustrated by step B of the drawing, the next step in the process is to create a second plurality of tubular parisons from a polymeric material different from the first. The material is again selected for physical properties that synergistically combine with the physical properties of the first tubular parison. Here again, the second tubular parison 12 may be formed by extruding same to a desired outer diameter which is slightly less than the I.D. of the first tubular parison. The extrusion may then be cut to a predetermined lengths which may be equal to or less than the lengths of the first tubular parisons.

As was the case with the formation of the first tubular parisons, rather than extruding a tube to the desired I.D., it may be somewhat oversized and then placed on a mandrel having an O.D. equal to the desired I.D. of the second tubular parisons and then necked down in a stretching operation until it conforms to the O.D. of the mandrel and is of the desired wall thickness. The mandrel can then be removed and the tube cut to yield plural parisons of the designed length. The wall thickness of the second parisons may typically be in the range of from 0.005 to 0.015 inch, again with a thickness variation of under 10% and preferably between 0% and 3%.

Once the first and second parisons are formed, one of each are coaxially disposed in overlapping relationship as shown in Step C of FIG. 2 so that the first tubular parison surrounds the second. While the process thus far described contemplates only two coaxially disposed tubular parisons, those skilled in the art can appreciate that the method can be extended to three or more layers by merely creating additional tubular parisons of an appropriate size so that they can be telescopingly disposed relative to one another in a predetermined order. For example, if the polymeric materials chosen for the first and second tubular parisons tend not to bond well to one another, a third parison, compatible with each, can be formed and dimensioned so as to fit between the outermost and innermost parisons when the three are telescopingly disposed relative to one another.

As is reflected by step D in the flow chart, the composite parison of step C is heated to a temperature that is above the transition temperatures of the polymeric materials selected for the inner and outer layers. The heating step may be accomplished within or external to the mold 14 (FIG. 2) used in carrying out step E of the process. In step E, the product of step D is subjected to a stretch/blow-molding operation commonly used in creating single layer angioplasty expander members. Because of the coaxial disposition of the first and second tubular parisons, during the stretch/blow-molding operation, a multi-layer expander member of a predetermined length, O.D., and wall thickness results. That expander member exhibits the physical properties that are a combination of those of the chosen polymeric materials and their relative coaxial position relative to one another.

As those skilled in the art appreciate, all elements of the composite parison are longitudinally and radially expanded during the stretch/blow-molding operation to biaxially orient the molecules thereof. This is conventionally accomplished by using a split mold 14 which permits the drawing or stretching of the composite parison in the longitudinal direction while, at the same time, injecting a suitable fluid, under pressure, to radially expand the materials so that they conform to the cavity of the mold. By properly establishing the wall thickness of the parison layers, the radial size of the mold cavity and the amount of longitudinal stretching employed, it is possible to create expander members having predetermined characteristics including burst strength, extensibility or compliance, O.D. and creep.

From what has been thus far described, it is apparent that a wide variety of polymeric materials may be selected for pre-forming the parisons. During production of balloons, different combinations and orientations of the pre-formed parisons can be selected to create composite expander members exhibiting desired properties. The ability to mix and match and thereby tailor the properties of the end product is an important advantage of the method of the present invention. Polymeric materials for the outermost parison include not only PET, but also Nylon, polyether block amide, polyethylene, polyurethane, polyvinyl chloride, polycaprolactam and N-vinyl-pyrrolidone polymer.

While the steps illustrated in FIGS. 1 and 2 involve only two separate parisons concentrically disposed relative to one another, it can be appreciated that additional layers may be added as well. For example, if it is desired to decrease the coefficient of friction of the outer exposed surface of the balloon, a tubular parison of a hydrophilic polymer such as polycaprolactam, and vinyl pyrrolidone may be pre-formed and then fitted over the assembly of Step C before the resulting composite parison is heated and stretch blow-molded as in Steps D and E. The polymer of one of the intermediate layers would typically be selected for its tensile properties and, without limitation, may consist essentially of a material selected from the group including ABS (acrylonitrile-butadiene-styrene), ABS/Nylon, ABS/PBC, ABS/polycarbonate and combinations thereof, acrylonitrile copolymer, polyacrylamide, polyacrylate, polyacrylsulfone, polyethylene terephthalate (PET), polybutylene terephthalate (PBT), polyethylene naphthalate (PEN), liquid crystal polymer (LCP), polyester/polycaprolactone, polyester/polyadipate, polyetheretherketone (PEEK), polyethersulfone (PES), polyetherimide (PEI), polyetherketone (PEK), polymethylpentene, polyphenylene ether, polyphenylene sulfide, styrene acrylonitrile (SAN), Nylon 6, Nylon 4/6, Nylon 6/6, Nylon 6/66, Nylon 6/9, Nylon 6/10, Nylon 6/12, Nylon 11 and Nylon 12. layer may be selected for abrasion-resistance and may comprise Nylon 6, Nylon 12, Nylon 6/6 a polyurethane polyhpenylene or a polyamide copolymer.

If the inner layer resulting from the coaxially arranged parison is intended to enhance the bonding characteristics of the resulting balloon to a catheter body, it may comprise a plastic material selected from the group consisting of ethylene propylene copolymer, ethylene vinyl acetate polymer (EVA), and ethylene vinyl alcohol polymer (EVOH), various ionomers, polyethylene type I–IV, polyolefins, polyurethane, polyvinyl chloride and polysiloxanes (silicons). The inner layer may also comprise a material selected from the group including polyethylene terephthalate, acrylonitrile-butadiene-styrene (ABS) and ABS/polycarbonate copolymers.

It can be appreciated that the process of the present invention can be used to combine a variety of materials, each having distinct physical properties, e.g. one for its burst strength and distensibility, another for its bondability to a range of different plastics, another for its lubricity and freedom from pinholes, etc.

The process outlined in the steps of FIGS. 1 and 2 can be slightly modified in creating a multi-layer parison by simultaneously necking down separate, multiple extruded telescoping tubes of different polymers onto a common mandrel having an outside diameter equal to the inside diameter required of the composite parison from which the balloon is to be blown. That assembly is heated in a way to ensure adhesion of the different layers over the entire length that is to be used in the expander blowing step, i.e., the entire parison length that will be gripped, stretched and blown.

In a different process, one or more relatively short sleeves of a selected polymeric material is/are slipped over the outside of a longer base parison. The length of the sleeve is such that it occupies only the balloon blowing cavity of the split mold 14 used in the stretch/blow-molding step. The heat and radial pressure of the blowing process is used to ensure adhesion of the sleeve or sleeves to one another and to the base parison. Thus, a base parison is crated by extruding a tube to a desired I.D. and O.D. or by necking down a tube onto a mandrel whose outside diameter is equal to the desired inside diameter of the parison being formed and until the wall thickness thereof reaches a desired value. The mandrel is then removed and a pre-formed, relatively short, tubular sleeve is fitted over the base parison before the resulting composite is inserted into the mold in which the stretch blow-molding operation is to take place. Again, the mold is heated to the desired transition point for the polymers involved and the base parison is drawn longitudinally and a fluid is injected into it to radially expand the base parison and with it, the surrounding sleeve, to cause them to conform to the walls of the cavity formed in the mold. Again, those skilled in the art can appreciate that more than one sleeve can be concentrically disposed about the base parison to appropriately tailor the physical properties of the resulting catheter expander member.

This invention has been described herein in considerable detail to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method of manufacturing a multi-layer expander member for an angioplasty catheter comprising the steps of:
   a) preforming a first tubular parison of a polymeric material having first physical properties;
   b) preforming a second tubular parison of a polymeric material having second physical properties;
   c) later disposing one of said first and second preformed tubular parisons over the other of said first and second preformed tubular parisons to form a composite parison;
   d) heating said composite parison to a predetermined temperature; and
   e) blow-molding said composite parison in a mold having a cavity of a predetermined length and radial dimension to bond the polymeric material comprising the first tubular parison to the polymeric material comprising the second tubular parison in forming said multi-layer expander member.

2. The method as in claim 1 and further including the step of longitudinally stretching said composite parison simultaneously with the blow molding thereof.

3. The method as in claim 1 wherein said first tubular parison has a wall thickness in the range of from 0.018 and 0.030 inch and said second tubular parison has a wall thickness in the range of from 0.005 to 0.015 inch.

4. The method as in claim 3 wherein a variation in wall thickness over the length of each of said first and second parisons is under 10 percent.

5. The method as in claim 4 wherein said variation in wall thickness of said first and second parisons is between 3 percent and 0 percent.

6. The method as in claim 1 wherein said first tubular parison is formed from a polyester material and said second tubular parison is a polyamide.

7. The method as in claim 1 wherein said first tubular parison is polyethylene terethphalate and said second tubular parison is an abrasion resistant polymer material.

8. The method as in claim 7 wherein said abrasion resistant polymer material is selected from the group consisting of Nylon 6, Nylon 12, Nylon 6/6, polyethylene, polyurethane and a polyamide copolymer.

9. The method as in claim 1 wherein said second tubular parison comprises a tubular sleeve shorter in length than said first tubular parison.

10. The method as in claim 9 wherein said tubular sleeve is of a length equal to the predetermined length of the cavity of the mold.

11. The method as in claim 10 wherein a fluid is introduced under pressure into said first tubular member in said blow-molding step to radially expand said first tubular parison into intimate contact with said tubular sleeve to fuse the two together.

12. The method of claim 1 and further including the steps of:

a) forming a tubular member of a polymeric material thermally bondable to said first and second tubular parisons; and b) concentrically disposing said tubular member between said first preformed tubular parison and said second preformed tubular parison prior to the blow-molding step.

13. The method of claim 12 wherein said polymeric material of said tubular member is selected from the group consisting of ethylene propylene copolymer, ethylene vinyl acetate polymer, ethylene vinyl alcohol polymer, polysiloxane, polyethylene and copolymers thereof, polyolefin, polyurethane, polyvinyl chloride, polychorotriethylene, ethyl tetrafluoroethylene polymer, and polyamide.

14. A method of manufacturing a multilayer expander member for an angioplasty catheter comprising the steps of:

a) placing separately prepared inner and outer polymer tubes in telescoped relation with one another onto a cylindrical mandrel having a predetermined outer diameter, each polymer being of differing physical properties;

b) simultaneously stretching said inner and outer polymer tubes until said inner tube conforms to said outer surface of said cylindrical mandrel to provide a predetermined total wall thickness for said inner and outer polymer tubes;

c) removing said inner and outer polymer tubes from said mandrel yielding a composite parison, said composite parison having a lumen corresponding to said outer diameter of said mandrel;

d) heating said composite parison to a predetermined temperature; and e) expanding said composite parison both longitudinally and radially within a mold to biaxially orient and bond the polymer material comprising said inner and outer polymer tubes together.

15. The method as in claim 14 wherein said step of expanding said composite parison radially comprises injecting a fluid under pressure into said lumen.

16. The method as in claim 14 wherein said step of expanding said composite parison both longitudinally and radially includes simultaneously injecting a fluid under pressure into said lumen and longitudinally stretching said composite parison.

17. The method of claim 14 wherein said inner polymer tube is formed from a thermoplastic selected from the group consisting of polyethylene terephthalate, acrylonitrile-butadiene-styrene (ABS), ABS/polycarbonate.

18. The method of claim 14 wherein said outer polymer tube is formed from a thermoplastic selected from the group consisting of nylon, polyether block amide, polyethylene, polyurethane, polyvinyl, chloride, polycaprolactam, and N-vinyl-pyrrolidone polymer.

* * * * *